(12) United States Patent
Dal Farra et al.

(10) Patent No.: US 8,962,565 B2
(45) Date of Patent: Feb. 24, 2015

(54) PEPTIDES INVOLVED IN THE SCF C-KIT SIGNALING PATHWAY AND COMPOSITIONS COMPRISING SAME

(75) Inventors: Claude Dal Farra, Kerhonkson, NY (US); Nouha Domloge, Valbonne (FR); Jean-Marie Botto, Valbonne (FR)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 13/982,386

(22) PCT Filed: Jan. 30, 2012

(86) PCT No.: PCT/FR2012/000035
§ 371 (c)(1),
(2), (4) Date: Jul. 29, 2013

(87) PCT Pub. No.: WO2012/104500
PCT Pub. Date: Aug. 9, 2012

(65) Prior Publication Data
US 2014/0037560 A1    Feb. 6, 2014

(30) Foreign Application Priority Data

Feb. 1, 2011    (FR) .................................... 11 00299

(51) Int. Cl.
| | | |
|---|---|---|
| *A61K 38/08* | (2006.01) | |
| *A61K 8/64* | (2006.01) | |
| *C07K 7/06* | (2006.01) | |
| *C07K 7/08* | (2006.01) | |
| *A61Q 17/04* | (2006.01) | |
| *A61Q 19/02* | (2006.01) | |
| *A61Q 19/08* | (2006.01) | |
| *C07K 5/113* | (2006.01) | |
| *A61Q 19/00* | (2006.01) | |

(52) U.S. Cl.
CPC ................. *A61K 8/64* (2013.01); *C07K 5/1021* (2013.01); *C07K 7/06* (2013.01); *C07K 7/08* (2013.01); *A61Q 19/004* (2013.01); *A61Q 17/04* (2013.01); *A61Q 19/02* (2013.01); *A61Q 19/08* (2013.01); *A61K 38/08* (2013.01)
USPC ....... 514/18.8; 514/21.6; 514/21.7; 514/21.8; 514/21.9; 530/327; 530/328; 530/329; 530/330; 424/59; 424/62

(58) Field of Classification Search
CPC ......... A61K 38/08; A61K 8/64; A61Q 17/04; A61Q 19/02; A61Q 19/004; A61Q 19/08; C07K 7/06; C07K 7/08
USPC .................... 514/18.8, 21.6, 21.7, 21.8, 21.9; 530/327, 328, 329, 330; 424/59, 62
See application file for complete search history.

(56) References Cited

U.S. PATENT DOCUMENTS

| | | | | |
|---|---|---|---|---|
| 6,919,187 | B2 * | 7/2005 | Bhatia et al. ................. | 435/69.1 |
| 7,300,918 | B2 * | 11/2007 | Rath ............................... | 514/7.4 |
| 8,440,881 | B2 * | 5/2013 | Park et al. ..................... | 800/290 |
| 2002/0146776 | A1 * | 10/2002 | Bhatia et al. ................. | 435/69.3 |
| 2011/0311538 | A1 * | 12/2011 | Schlessinger et al. ...... | 424/138.1 |
| 2013/0333061 | A1 * | 12/2013 | Wu et al. ....................... | 800/260 |
| 2014/0010861 | A1 * | 1/2014 | Bancel et al. ................ | 424/450 |
| 2014/0106981 | A1 * | 4/2014 | Hood et al. .................... | 506/9 |
| 2014/0130203 | A1 * | 5/2014 | La Rosa et al. .............. | 800/278 |

FOREIGN PATENT DOCUMENTS

| | | |
|---|---|---|
| JP | 2008-031094 | 2/2008 |
| WO | 93/20210 | 10/1993 |
| WO | 01/31019 | 5/2001 |
| WO | 2010/037395 | 4/2010 |

OTHER PUBLICATIONS

PCT, International Search Report, International Application No. PCT/FR2012/000035 (mailed Jun. 5, 2012, published Aug. 9, 2012).

* cited by examiner

*Primary Examiner* — Julie Ha
(74) *Attorney, Agent, or Firm* — Thompson Hine L.L.P.

(57) ABSTRACT

Peptide compounds of general formula (I) $R_1\text{-}(AA)_n\text{-}X_1\text{—}X_2\text{—}X_3\text{-}Asp\text{-}Leu\text{-}Lys\text{-}Lys\text{-}X_4\text{—}X_5\text{-}(AA)_p\text{-}R_2$, cosmetic or pharmaceutical compositions comprising at least one peptide compound of general formula (I) in a physiologically acceptable medium, and methods for cosmetic treatment of skin are disclosed. The peptide compounds of general formula (I) were demonstrated to be agents making it possible to influence the pigmentation of the skin and skin appendages, by ensuring optimal transfer of the melanosomes to the keratinocytes, so as to make the skin tone uniform owing to an effect on the SCF/c-Kit signaling pathway. The compounds, compositions, and methods treat or attenuate age-related pigmentation defects and the effects of photoaging on the skin.

18 Claims, 3 Drawing Sheets

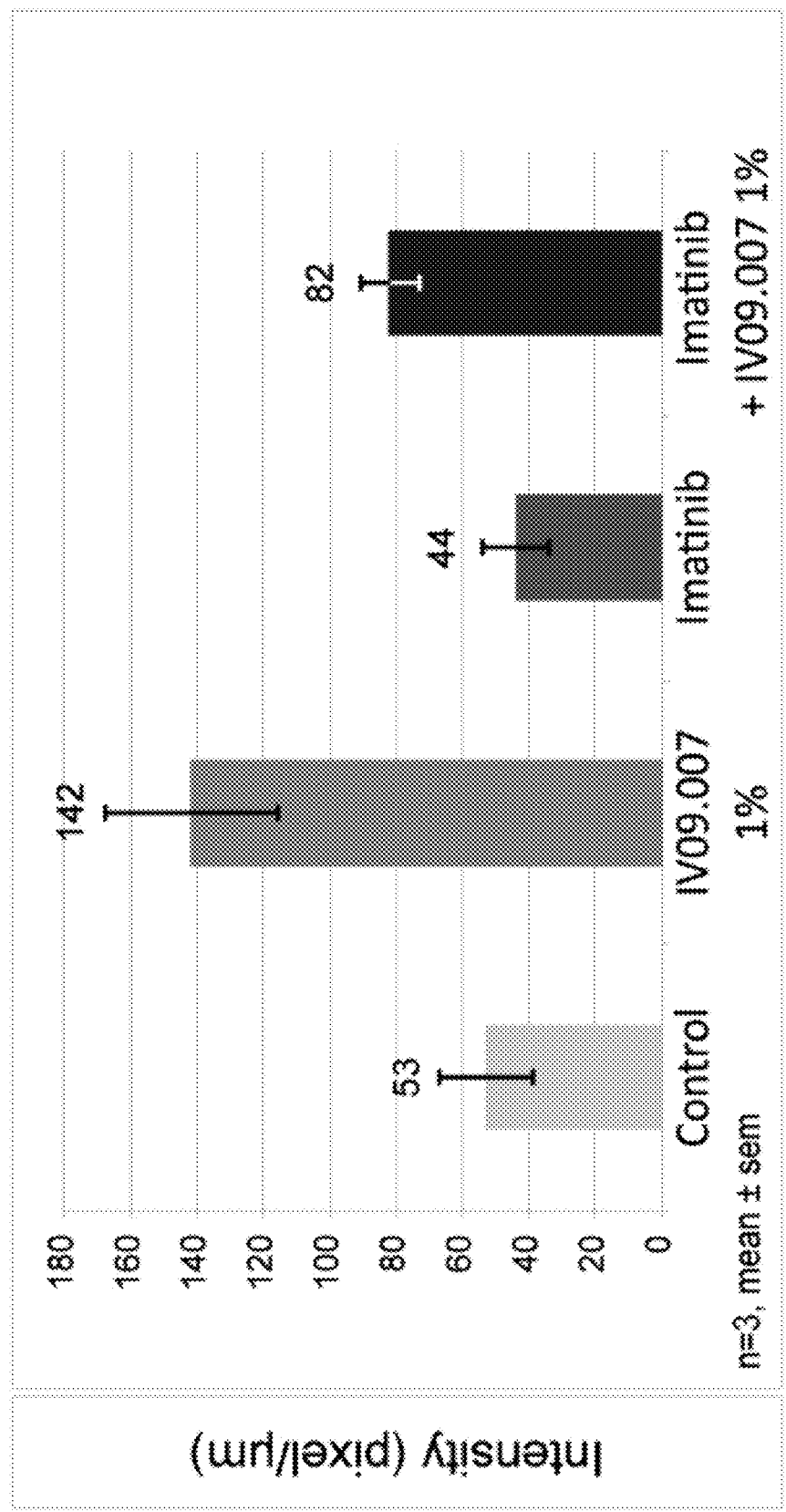
Figure 1: quantification of the melanin content of skin biopsies treated with the peptide SEQ ID n°6 and imatinib for 48 h

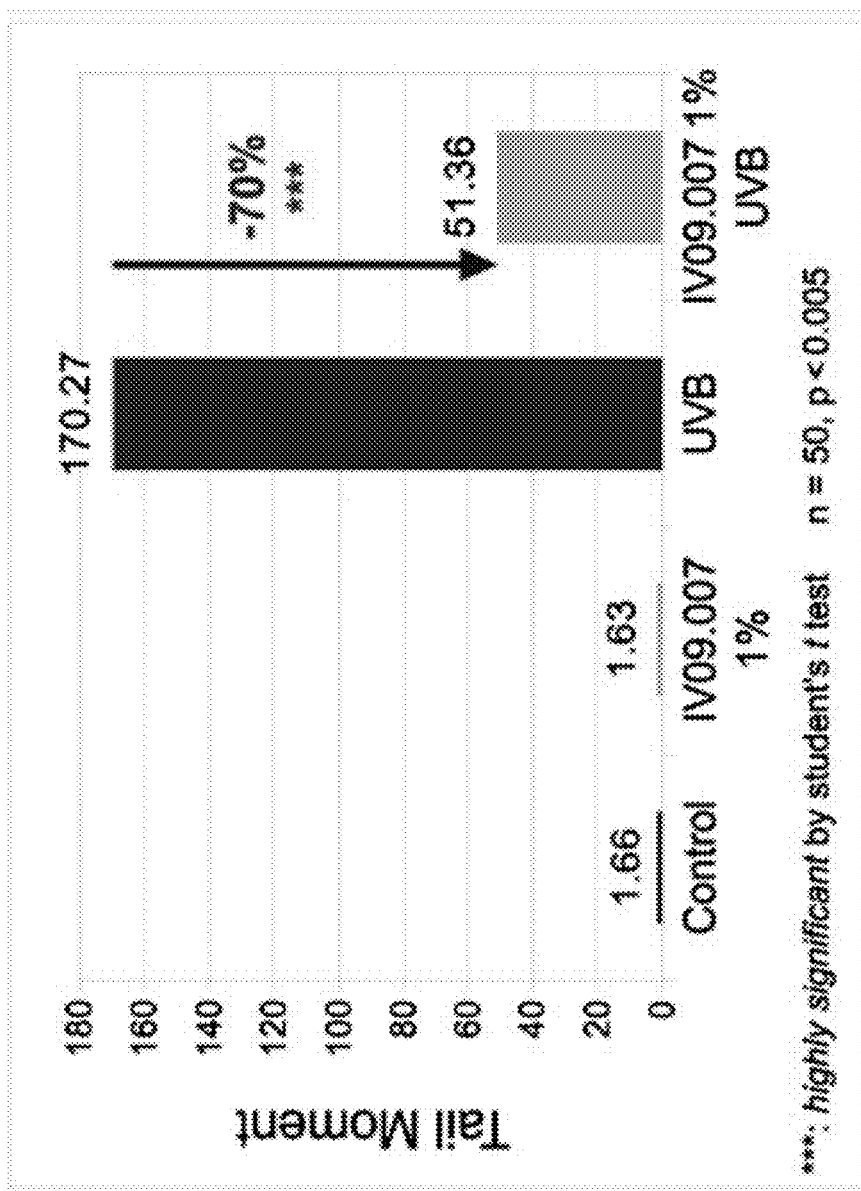
Figure 2a: Comet assay on NHK treated with the peptide SEQ ID n°7 and irradiated with UVB radiation

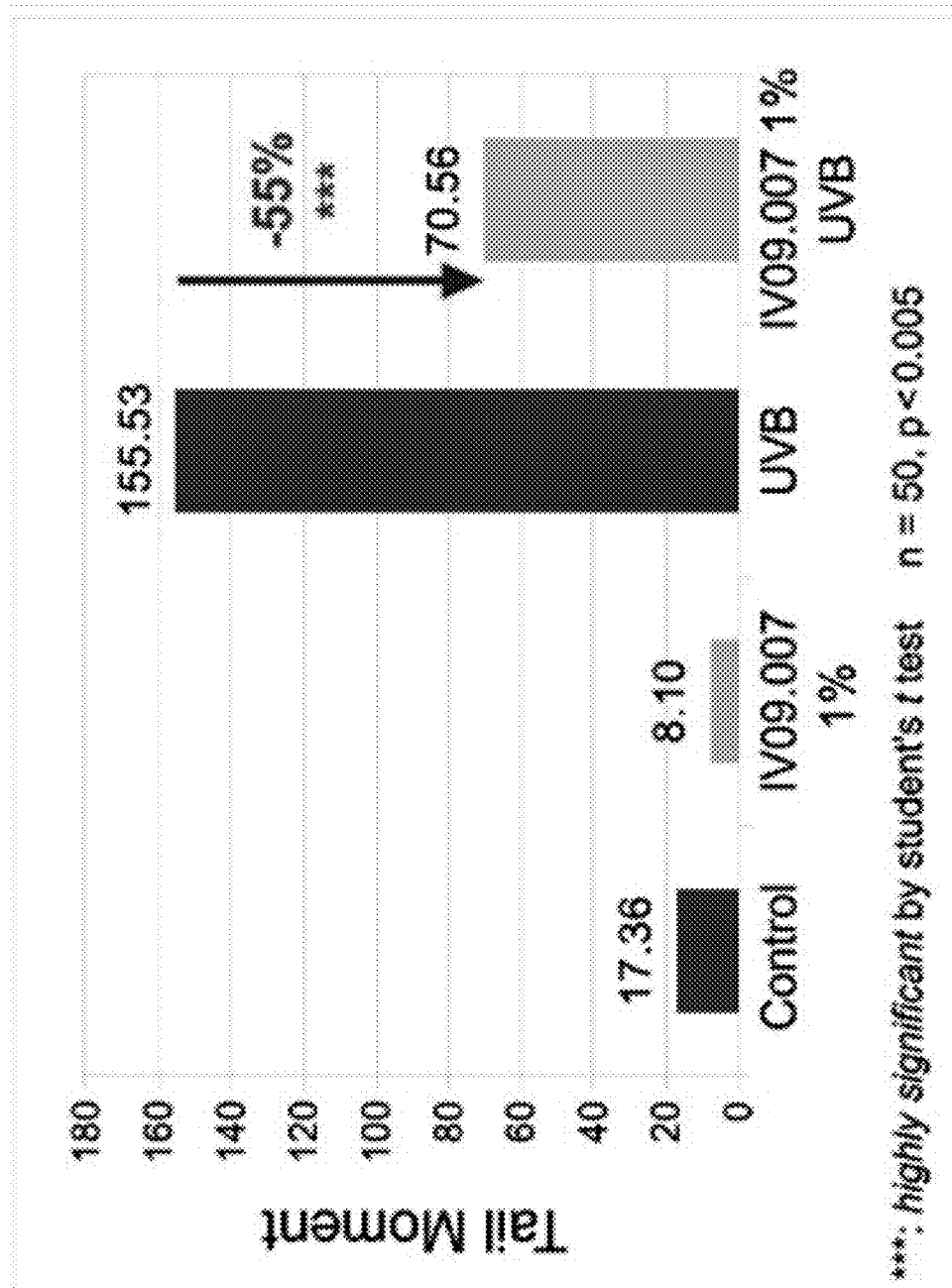
Figure 2b: Comet assay on NHEM treated with the peptide SEQ ID n°7 and irradiated with UVB radiation

PEPTIDES INVOLVED IN THE SCF C-KIT SIGNALING PATHWAY AND COMPOSITIONS COMPRISING SAME

This invention relates to the fields of cosmetics and pharmacy. It relates to peptide compounds with the following general formula (I):

$R_1$-$(AA)_n$-$X_1$—$X_2$—$X_3$-Asp-Leu-Lys-Lys-$X_4$—$X_5$-$(AA)_p$-$R_2$ as a compound having an action on the SCF/c-Kit signaling pathway, as well as its uses in cosmetic and/or pharmaceutical compositions in order to attenuate skin pigmentation defects.

In humans, hair and skin color is related to individual factors (ethnic origin, sex, age, etc.) and environmental factors (in particular the seasons of the year, region inhabited, etc.). It is primarily determined by the nature and concentration of melanin produced by the melanocytes. The melanocytes are large dendritic cells located in the basal layer of the epidermis. These specialized cells will, by way of specific organites, the melanosomes, synthesize melanin. The synthesis of melanin or melanogenesis is a complex process of which the precise mechanisms are not yet understood, and which schematically involves the following steps:

Tyrosine→Dopa→Dopaquinone→Dopachrome→Melanin.

This melanin plays a fundamental role in the determination of skin color. We often hear of epidermal (or elementary) melanization units that correspond in fact to functional groups in which the melanocytes maintain contact with a certain number of neighboring keratinocytes, to which they transfer the pigment grains. The number of units varies according to the body region. These units contain, on average, 1 melanocyte for 36 keratinocytes (although there are variations). The transfer of pigment from the melanocyte to the keratinocytes occurs in 4 main steps:

1: synthesis of the melanosomes in the melanocyte;
2: melanization of the melanosomes in the melanocyte;
3: transfer of the melanosomes to the keratinocytes;
4: degradation and elimination of melanosomes in the keratinocytes.

As the melanin is synthesized in the melanosomes, they move from the perinuclear region to the end of the dendrites of the melanocytes. By phagocytosis, the end of the dendrites is captured by the keratinocytes, the membranes are degraded and the melanosomes are redistributed in the keratinocytes. Once in the keratinocytes, the melanosomes are distributed according to their size: in isolation for the largest ones, in groups for the smallest ones (Ortonne, et al. 1981). They are secondarily degraded in lysosomal vacuoles (Fitzpatrick et al. 1979).

The transfer of melanosomes to the keratinocytes, as described above, is performed by means of numerous biological, enzymatic processes, and is not currently fully understood. One of the players in this melanosome transfer process is SCF protein and its c-Kit receptor. The SCF (Stem Cell Factor) protein is the natural agonist ligand of the c-Kit receptor, which is a member of the sub-family III of the superfamily of receptor tyrosine kinases (RTK). It has been demonstrated in numerous publications that this SCF/c-Kit signaling pathway played a key role in a number of biological processes, and in particular in hematopoiesis, spermatogenesis, as well as in the maintenance of homeostasis of the skin and in the pigmentation of same (Longley J. et al, *J Invest Dermatol.* 1999; 113: 139-140).

It is known that anomalies in the transfer of melanosomes to the keratinocytes can lead to pigmentation disorders, whether of the hyperpigmentation or the hypopigmentation type. More specifically, certain studies have shown that the SCF/c-Kit signaling pathway could regulate both the proliferation and the differentiation of melanocytes. The SCF protein at the surface of the epidermal keratinocytes could enable regulation of the adjacent melanocytes, via direct interaction with the c-Kit receptor located on said melanocytes. Moreover, it has been demonstrated that certain transcription factors crucial for the synthesis of melanin were activated by the SCF/c-Kit pathway (Grichnik, J M et al. *J Invest Dermatol.* 1998; 111: 233-238). It can therefore be considered that the SCF/c-Kit pathway is important for the normal function of melanocytes, and that it is possible for alterations at the level of this signaling pathway are responsible for certain melanocyte disorders, i.e. pigmentation disorders.

Along this line of research, the Applicant demonstrated that peptide compounds of the following general formula (I):

$$R_1\text{-}(AA)_n\text{-}X_1\text{—}X_2\text{—}X_3\text{-Asp-Leu-Lys-Lys-}X_4\text{—}X_5\text{-}(AA)_p\text{-}R_2 \quad (I)$$

were agents making it possible to influence the pigmentation of the skin and skin appendages, by ensuring optimal transfer of the melanosomes to the keratinocytes, so as to make the skin tone uniform owing to an effect on the SCF/c-Kit signaling pathway.

The peptide compounds according to the invention are characterized by the fact that they:

protect the pigment structures of the skin from external stresses;

make it possible to attenuate age-related pigmentation defects as well as the effects of photoaging on the skin; and make it possible to treat skin tone irregularities and unify skin tone.

This invention therefore relates firstly to a peptide compound with the following general formula (I):

$$R_1\text{-}(AA)_n\text{-}X_1\text{—}X_2\text{—}X_3\text{-Asp-Leu-Lys-Lys-}X_4\text{—}X_5\text{-}(AA)_p\text{-}R_2 \quad (I)$$

This invention relates secondly to a cosmetic composition comprising, as an active principle, said peptide compound of formula (I).

In addition, this invention relates thirdly to the use of a cosmetic composition comprising said peptide compound of formula (I) in order (i) to protect the skin pigment structures from external stresses, (ii) to attenuate age-related pigmentation defects and the effects of photoaging on the skin, and (iii) to treat skin tone irregularities and unify skin tone.

Finally, this invention relates fourthly to a method for cosmetic treatment of the skin or skin appendages to be treated by means of the composition comprising said peptide compound of formula (I).

This invention relates, firstly, to a peptide compound of general formula (I):

$$R_1\text{-}(AA)_n\text{-}X_1\text{—}X_2\text{—}X_3\text{-Asp-Leu-Lys-Lys-}X_4\text{—}X_5\text{-}(AA)_p\text{-}R_2 \quad (I)$$

wherein, $X_1$ represents an asparagine, a serine, a glutamine or no amino acid, $X_2$ represents a serine, a threonine, a cysteine or no amino acid, $X_3$ represents an arginine, a lysine, a histidine or no amino acid, $X_4$ represents a serine, a tyrosine, a threonine or no amino acid, $X_5$ represents a phenylalanine, a proline, an alanine, a valine or no amino acid, AA represents any amino acid, and n and p are integers between 0 and 2, $R_1$ represents the primary amino function of the N-terminal amino acid, —$NH_2$, wherein one of the two hydrogen atoms can be substituted either by a $C_1$ to $C_{30}$ saturated or unsaturated alkyl chain of the acetyl type, or by an aromatic group of the benzoyl, tosyl or benzyloxycarbonyl type.

$R_2$ represents the hydroxyl group of the carboxyl function of the C-terminal amino acid, —OH, wherein the hydrogen atom can be substituted by a $C_1$ to $C_{30}$ alkyl chain, or an $NH_2$, NHY or NYY group, in which Y represents a $C_1$ to $C_4$ alkyl chain, said sequence of general formula (I) consisting of 4 to 13 amino acid residues.

The term "peptide compound" or "peptide" refers to a chain of two or more amino acids bound together by peptide bonds or by modified peptide bonds.

"Peptide compound" or "peptide" should be understood to mean the natural or synthetic peptide of the invention as described above, or at least one of its fragments, whether it is obtained by proteolysis or synthetically, or any natural or synthetic peptide of which the sequence consists entirely or partially of the sequence of the aforementioned peptide.

The amino acids constituting the peptide compound according to the invention can be in a levorotatory configuration, i.e. L-, and/or a dextorotatory configuration, i.e. D-. The peptide according to the invention can therefore be in L-, D- or DL-form.

To improve resistance to degradation, it may be necessary to use a protected form of the peptide according to the invention. The form of protection must obviously be a biologically compatible form and must be compatible with a use in the fields of cosmetics and pharmacy. Preferably, to protect the primary amine function of the N-terminal amino acid, a substitution by an $R_1$ group of the acyl type having a saturated or unsaturated $C_1$ to $C_{30}$ alkyl chain, capable of being chosen from an acetyl group or an aromatic group, is used. Preferably, to protect the carboxyl function of the C-terminal amino acid, a substitution by an $R_2$ group of the $C_1$ to $C_{30}$ alkyl chain type or an $NH_2$, NHY or NYY group with Y representing a $C_1$ to $C_4$ alkyl chain.

The peptide according to the invention can be protected at the N-terminal end, the C-terminal end or at both ends.

In a first embodiment of the invention, in general formula (I), n and p are equal to zero and the sequence of general formula (I) consists of 4 to 9 amino acid residues. This therefore means that, in general formula (I):

$X_1$ represents an asparagine, a serine, a glutamine or no amino acid, $X_2$ represents a serine, a threonine, a cysteine or no amino acid, $X_3$ represents an arginine, a lysine, a histidine or no amino acid, $X_4$ represents a serine, a tyrosine, a threonine or no amino acid, $X_5$ represents a phenylalanine, a proline, an alanine, a valine or no amino acid, the integers n and p are equal to zero, $R_1$ represents the primary amine function of the N-terminal amino acid, —$NH_2$, wherein one of the two hydrogen atoms can be substituted either by a saturated or unsaturated $C_1$ to $C_{30}$ alkyl chain of the acetyl type, or by an aromatic group of the benzoyl, tosyl or benzyloxycarbonyl type, $R_2$ represents the hydroxyl group of the carboxyl function of the C-terminal amino acid, —OH, wherein the hydrogen atom can be substituted by a $C_1$ to $C_{30}$ alkyl chain, or an $NH_2$, NHY or NYY group, wherein Y represents a $C_1$ to $C_4$ alkyl chain, said sequence of general formula (I) consisting of 4 to 9 amino acid residues.

In a second preferred embodiment, the peptide compound corresponds to one of the following formulas:

```
                                               (SEQ ID NO: 1)
Ser-Cys-Arg-Asp-Leu-Lys-Lys-Thr-NH2

(SEQ ID NO: 2)
Asn-Ser-Ser-Lys-Asp-Leu-Lys-Lys-Phe-Val-Ala (SEQ ID NO: 3)
Cys-Lys-Asp-Leu-Lys-Lys-Ser-Phe (SEQ ID NO: 4)
Gln-Thr-Arg-Asp-Leu-Lys-Lys-Ser-Pro-Lys-Val-NH2

(SEQ ID NO: 5)
Asn-Lys-Asp-Leu-Lys-Lys-Pro-Met (SEQ ID NO: 6)
His-Asp-Leu-Lys-Lys-Tyr-NH2

(SEQ ID NO: 7)
Asp-Leu-Lys-Lys-NH2
```

The invention also relates to homologous forms of these sequences. The term "homologous" refers, according to the invention, to any peptide sequence identical to at least 50%, or preferably at least 80%, and even more preferably to at least 90% of said peptide sequence, chosen from sequences SEQ ID NO: 1 to SEQ ID NO: 7. "Peptide sequence identical to at least X %" means a percentage of identity between the amino acid residues of the two sequences to be compared, obtained after optimal alignment of the two sequences. The optimal alignment is obtained by means of local homology algorithms such as those used by the BLAST P computer software program available at the NCBI site.

The term "homologous" can also refer to a peptide that differs from the sequence of a peptide of sequence SEQ ID NO: 1 to SEQ ID NO: 7 by the substitution of chemically equivalent amino acids, i.e. by the substitution of a residue by another one having the same characteristics. Thus, the classic substitutions are made between Ala, Val, Leu and Ile; between Ser and Thr; between the acid residues Asp and Glu; between Asn and Gln; and between the basic residues Lys and Arg; or between the aromatic residues Phe and Tyr.

The peptide of general formula (I) according to the invention can be obtained either by classic chemical synthesis (in solid phase or in homogeneous liquid phase), or by enzymatic synthesis (Kullmann et al., J. Biol. Chem. 1980; 225: 8234) using its constituent amino acids or derivatives.

The peptide according to the invention can be of natural or synthetic origin. Preferably, according to the invention, the peptide is obtained by chemical synthesis.

Finally, the active principle can be a single peptide, a mixture of peptides or peptide derivatives and/or consist of amino acid derivatives.

The peptide compound according to the invention can be used as a drug.

According to an advantageous embodiment of the invention, the peptide compound according to the invention is solubilized in one or more physiologically suitable solvents, classically used by a person skilled in the art, such as water, glycerol, ethanol, propanediol, butylene glycol, dipropylene glycol, ethoxylated or propoxylated diglycols, cyclic polyols, or any mixture of these solvents.

According to yet another advantageous embodiment of the invention, the peptide compound according to the invention is solubilized in a cosmetic or pharmaceutical vector such as liposomes, or adsorbed on powdery organic polymers, mineral supports such as talcs and bentonites, and more generally solubilized in, or fixed on, any physiologically suitable vector.

This invention relates, secondly, to a cosmetic composition comprising, as an active principle, said peptide compound of general formula (I).

Preferably, the compositions according to the invention are in a form suitable for topical application comprising a cosmetically acceptable medium. By "cosmetically acceptable", we mean media that are suitable for use in contact with the skin or human skin appendages, without risk of toxicity, incompatibility, instability, allergic response or the like. The compositions intended to be applied to the skin can be in the form of a cream, an oil-in-water emulsion, or a water-in-oil or multiple emulsion, a solution, a suspension, a microemulsion, an aqueous or anhydrous gel, a serum, or a vesicle dispersion, a patch, a spray, an ointment, a pomade, a lotion, a colloid, a milk, a lotion, a stick or a powder, all suitable for application on the skin, lips and/or skin appendages.

Preferably, said peptide compound is present in the composition at a concentration of between around 0.0005 and 500 ppm, and preferably at a concentration of between 0.01 and 5 ppm.

Even more preferably, the composition according to the invention also contains at least one other active principle. It is possible to cite, in a non-limiting manner, the following classes of ingredients: other active peptide agents, plant extracts, healing, anti-aging, anti-wrinkle, soothing, anti-free radical and anti-UV agents, hydrating, anti-inflammatory and anesthetic agents, agents modulating differentiation, skin pigmentation or depigmentation, etc.

In a more specific embodiment, the composition according to the invention will comprise, in addition to the peptide compound of formula (I):
  one (or more) cytochrome c-activating compound, and/or;
  one (or more) aquaporin-activating compound and/or;
  one (or more) sirtuin-activating compound and/or;
  one (or more) compound that increases cell adhesion and/or;
  one (or more) compound that increases the production of matrix proteins of the collagen or laminin type, etc.;
  one (or more) hsp protein-modulating compound;
  one (or more) compound that increases cell energy;
  one (or more) pigmentation-modulating compound such as a yeast, amaranth, linseed, bean, cacao, corn, soy, sunflower, rapeseed or pea peptide extract;
  one (or more) compound improving the skin barrier function;
  one (or more) mitochondria-protecting compound.
Said compounds above can be natural, such as plant peptide hydrolysates, or of synthetic origin, such as peptide compounds.

In addition, additives such as solvents, diluents, dyes, sunscreens, self-tanning agents, pigments, fillers, preservatives, odor absorbents, thickening agents, emulsifiers, moistening agents, emollients, fragrances, antioxidants, film-forming agents, chelating agents, sequestering agents and conditioners can be added to the composition.

In every case, a person skilled in the art will make sure that these adjuvants as well as the proportions thereof are chosen so as not to adversely affect the desired advantageous properties of the composition according to the invention. These adjuvants can be, for example, between 0.01 and 20% of the total weight of the composition. When the composition of the invention is an emulsion, the fatty phase can be 5 to 80% by weight, and preferably 5 to 50% by weight with respect to the total weight of the composition. The emulsifiers and co-emulsifiers used in the composition will be chosen among those classically used in the field considered. For example, they may be used in a proportion ranging from 0.3 to 30% by weight with respect to the total weight of the composition.

The invention relates, thirdly, to the use of a cosmetic composition comprising said peptide compound in a cosmetically acceptable medium for protecting skin pigment structures from external stresses. By "pigment structures", we mean the melanocytes and keratinocytes maintaining contact with one another and forming an epidermal (or elementary) melanization unit (more precisely one melanocyte for 36 keratinocytes, on average).

By "external stresses", we mean stresses that the environment may product. For example, it is possible to cite stresses such as pollution, UV radiation, stresses causing oxidative stress, or irritating products such as surfactants, preservatives or fragrances, mechanical stresses, such as abrasions, shaving or hair removal. However, preferably, the external stresses consist primarily of UV radiation, and in particular UVB radiation, and the stresses causing oxidative stress.

Another use of the peptide according to the invention consists of attenuating age-related pigmentation defects and the effects of photoaging on the skin. By "photoaging", we mean premature skin aging caused by prolonged and cumulative exposure to the sun. By "age-related pigmentation defects", we mean age spots, solar lentigines, depigmentation spots or freckles. To this effect, the peptide according to the invention may be used to treat skin tone irregularities and unify skin tone.

Finally, the invention relates, lastly, to a method for cosmetic treatment characterized by applying, in the morning or the evening, on the skin, a composition comprising the peptide according to the invention in order to attenuate age-related pigmentation defects and the effects of photoaging on the skin. A first embodiment consists of applying said composition either before sun exposure, as before-sun care, or after sun exposure, as after-sun care, in order (i) to prevent and/or repair damage due to UV radiation on the skin cells and (ii) to limit the appearance of hyperpigmentation spots.

The following examples describe and demonstrate the efficacy of peptide compounds as described in the invention, but must not be interpreted as limiting the present invention.

FIG. 1 shows the results, in the form of histograms, of a quantification of the melanin intensity in biopsies of human skin treated or not treated with a peptide compound according to the invention and an SCF/c-Kit signaling pathway inhibitor.

FIGS. 2a and 2b are histograms showing the results of 2 comet assays performed on normal human keratinocytes (NHK) and normal human epidermal melanocytes (NHEM) subjected to UVB radiation and treated or not treated with a peptide compound according to the invention.

EXAMPLE 1

Fontana-Masson on Biopsies of Human Skin Treated or Not Treated with Peptide Compound of SEQ ID NO: 6 at 1% and a c-Kit Inhibitor Biopsies from human skin samples are placed in culture at the air/liquid interface. The biopsies are then kept in culture for 48 hours, treated or not treated with the peptide compound SEQ ID NO: 6 at 1%, at a rate of three applications per day and treated or not treated with a specific c-Kit activity inhibitor, imatinib, at a concentration of 20 $\mu$M at a rate of one application per day.

The biopsies are then fixed in formaldehyde, then embedded in paraffin. Sections of 4 μm are then produced and deposited on Superfrost Plus (Thermo Scientific) slides. The melanin on the sections is then stained by means of a 10% silver nitrate solution heated to 60° C. and developed by adding the 5% sodium thiosulfate solution. The skin sections are then examined under the microscope in the visible spectrum (Nikon Eclipse E600 microscope).

Results:

All of the results are shown in FIG. 1.

The intensity of the melanin in pixels/μm was measured under 4 conditions: control, with the active agent, with imatinib, and with the active agent and imatinib. When the active agent is added to the culture medium without inhibitor, an increase in the melanin intensity going from 53 to 142 pixels/μm with respect to the control condition is observed. Thus, the effect of the active agent on the melanin intensity is observed.

When the c-Kit inhibitor is added to the medium (without active agent), a drop in the melanin intensity, from 53 pixels/μm under control conditions to 44 pixels/μm, is observed. This thus confirms the inhibiting effect of imatinib on the amount of melanin present. When the imatinib is added to the culture medium in the presence of the peptide active agent, it is observed that the inhibiting effect of imatinib is reversed by the activating effect of the compound according to the invention, on the c-Kit signaling pathway. The melanin intensity goes from 44 pixels/μm under the condition with imatinib alone, to 82 pixels/μm under the condition with the peptide compound and imatinib.

Conclusions:

It is observed that after 48 hours of treatment, the peptide compound SEQ ID NO: 6 induces an increase in the melanin content in the basal layer of the epidermis and makes it possible to reverse the depigmenting effect caused by imatinib, thus suggesting a specific action of the peptide active agent on the signaling pathway involving c-Kit. The effects of the peptide compound according to the invention could therefore contribute to better protection of the basal layer of the epidermis.

EXAMPLE 2

Microarray Study of the Expression of a Selection of Genes in NHK Cells Treated or not Treated with the Peptide Compound SEQ ID NO: 3 at 1%

Normal human keratinocytes (or NHK) are placed in culture for 48 hours and are treated with the peptide compound SEQ ID NO: 3 at a concentration of 1%. A control condition without any active ingredient is also used.

The cells are then detached from their support by means of trypsin, then centrifuged at 1500 rpm for 10 minutes in order to concentrate them. The cells are resuspended in PBS 1× and 8 volumes of PreProtect (Miltenyi Biotec) in order to stabilize the RNAs. The total RNAs are then extracted and amplified using the μMACS One-step T7 Templates (Miltenyi Biotec) kit. The RNAs are reverse-transcribed and marked with fluorochromes Cy5 and Cy3. The fluorescent cDNA thus obtained are hybridized on slides, on which, in quadruplicate, genes expressed in the skin (PIQOR™ Skin Microarray) are deposited. This makes it possible to obtain the expression profile of these genes in the NHK cells treated or not treated with the peptide compound according to the invention. The data presented is obtained from a single pooled sample (n=1). A ratio above 1.48 indicates a positive regulation and a ratio below 0.58 shows a negative regulation. The characterization of the function of the genes is performed by using DAVID ("Database for Annotation, Visualization and Integrated Discovery") Bioinformatics Resources online software.

Results:

The results are presented in table 1 below.

TABLE 1 results of a microarray experiment on the expression of a selection of genes on NHK treated with the compound SEQ ID NO: 3 at 1% versus untreated NHK

| Genes: | | Ratios: |
|---|---|---|
| DNA repair and synthesis: | | |
| OGG1 | 8-OXOGUANINE DNA GLYCOSYLASE | 1.86 |
| MUTYH | A/G-SPECIFIC ADENINE DNA GLYCOSYLASE | 2.74 |
| RAD17 | CELL CYCLE CHECKPOINT PROTEIN RAD17 | 2.02 |
| RAD54L | DNA REPAIR AND RECOMBINATION PROTEIN RAD54-LIKE | 2.93 |
| XPA | DNA REPAIR PROTEIN COMPLEMENTING XP-A CELLS | 1.48 |
| ERCC2 | DNA EXCISION REPAIR PROTEIN ERCC-2 | 3.85 |
| ERCC5 | DNA REPAIR PROTEIN COMPLEMENTING XP-G CELLS | 1.52 |
| DDB2 | DNA DAMAGE BINDING PROTEIN 2 | 1.74 |
| TK1 | THYMIDINE KINASE, CYTOSOLIC | 1.92 |
| POLB | DNA POLYMERASE BETA | 1.60 |
| POLD1 | DNA POLYMERASE DELTA CATALYTIC CHAIN | 2.65 |
| POLD4 | DNA POLYMERASE DELTA SUBUNIT 4 | 2.42 |
| TYMS | THYMIDYLATE SYNTHASE | 1.77 |
| Immunologicals functions: | | |
| IL12B | INTERLEUKIN-12 BETA CHAIN PRECURSOR | 0.16 |
| IL13 | INTERLEUKIN-13 PRECURSOR | 0.20 |
| IL16 | INTERLEUKIN-16 PRECURSOR | 0.21 |
| IL17A | INTERLEUKIN-17 PRECURSOR | 0.07 |
| IL1A | INTERLEUKIN-1 ALPHA PRECURSOR | 0.52 |
| IL3 | INTERLEUKIN-3 PRECURSOR | 0.08 |
| IL5 | INTERLEUKIN-5 PRECURSOR | 0.12 |
| IL9 | INTERLEUKIN-9 PRECURSOR | 0.28 |
| Extracellular matrix and cutaneous barrier: | | |
| SPARC | SECRETED PROTEIN ACIDIC AND RICH IN CYSTEINE | 0.20 |
| TIMP2 | METALLOPROTEINASE INHIBITOR 2 PRECURSOR | 0.55 |
| LAMA5 | LAMININ ALPHA 5 CHAIN | 2.45 |

TABLE 1-continued results of a microarray experiment on the expression of a selection of genes on NHK treated with the compound SEQ ID NO: 3 at 1% versus untreated NHK

| Genes: | | Ratios: |
|---|---|---|
| MMP2 | MATRIX METALLOPROTEINASE-2 | 1.85 |
| KRT19 | KERATIN, TYPE I CYTOSKELETAL 19 | 1.57 |
| GLUL | GLUTAMINE SYNTHETASE | 1.78 |
| TGM1 | TRANSGLUTAMINASE 1 | 1.74 |
| Signal transduction and protein phosphorylation: | | |
| EGFR3 | EPIDERMAL GROWTH FACTOR RECEPTOR PRECURSOR | 1.56 |
| EGR1 | EARLY GROWTH RESPONSE PROTEIN 1 | 1.68 |
| PRKCG | PROTEIN KINASE C, GAMMA TYPE | 1.84 |
| PRKDC | DNA-DEPENDENT PROTEIN KINASE CATALYTIC SUBUNIT | 2.57 |
| PTK6 | PROTEIN TYROSINE KINASE 6 | 1.74 |
| MAP2K2 | MAP KINASE KINASE 2 | 1.62 |
| Cell death control: | | |
| BCL10 | B CELL LYMPHOMNLEUKEMIA 10 | 0.28 |
| BCL2L2 | BCL-2-LIKE 2 PROTEIN | 3.09 |
| DAD1 | DEFENDER AGAINST CELL DEATH 1 | 1.85 |
| Oxidative stress: | | |
| CAT | CATALASE | 1.80 |

Conclusions:

It is observed that certain genes involved in the reinforcement of the cutaneous barrier are modulated. An upward regulation of the genes involved in signal transduction is also observed. Finally, the expression of the catalase gene is increased, thus suggesting a protective effect against oxidative stresses.

EXAMPLE 3

Immunolabeling of the Expression of Catalase in Human Skin Biopsies Treated or not Treated with the Peptide Compound SEQ ID NO: 7

To confirm the results obtained in the microarray assay on the catalase gene, an immunolabeling of it was performed in the presence or absence of a peptide according to the invention.

For this, biopsies obtained from human skin samples are placed in culture at the air/liquid interface. The biopsies are then kept in culture and treated or not treated with the peptide compound SEQ ID NO: 7 at concentrations of 1 and 3%. These biopsies are then fixed in formaldehyde, then embedded in paraffin. 4-μm sections are produced and deposited on poly-lysine slides (Thermo Scientific). The immunolabeling is then performed by means of a rabbit polyclonal primary antibody, and specific to catalase (Calbiochem) then an anti-rabbit secondary antibody coupled to a fluorochrome (Invitrogen). The skin sections are then examined under the Epifluorescence microscope (Nikon Eclipse E600 microscope).

Results/Conclusions:

It is observed that the peptide SEQ ID NO: 7 according to the invention increases not only the expression of the catalase gene, but also the expression of the corresponding protein in the skin, which protein is essential in protection from oxidative stresses. Consequently, it can be concluded that the peptide SEQ ID NO: 7 has an effect on skin cell protection from oxidative stresses.

EXAMPLE 4

Comet Assay on NHK and NHEM Cells Treated with the Peptide Compound SEQ ID NO: 7 at 1% and Irradiated with UVB Radiation To observe the protective effect of the peptides according to the invention on NHK and NHEM cells and to confirm the results obtained by microarray, a comet assay is performed by subjecting said cells to UVB radiation.

For this, NHK and NHEM are placed in culture for 24 hours in the presence of the peptide compound SEQ ID NO: 7 at a concentration of 1%, then irradiated with UVB radiation in an amount of 30 mJ/cm$^2$ for NHEM and 60 mJ/cm$^2$ for NHK. A control condition is also used without a peptide active agent. The cells are then detached from their support by means of trypsin, then centrifuged at 900 rpm for 5 minutes in order to concentrate them and count them.

A defined number of cells (25,000 cells) is then embedded in a Low Melting agarose gel at 0.75%, then deposited on a glass slide previously coated with 1% agarose. The slides are then immersed in a lysis solution for 1 hour 30 minutes at 4° C., then in an alkaline solution for 20 minutes at 4° C. The cells are thus lyzed and the DNA is denatured. The slides are immersed in an electrophoresis solution before an electric field (20 V-250 mA) is applied. The DNA thus denatured is subjected to migration in the agarose gel at 4° C. The application of a fluorescent DNA dye on the slides (propidium iodide at 2 μg/ml) makes it possible to observe, under the microscope, DNA appearing in the form of comets if it has been damaged.

Finally, quantification software makes it possible to determine the Tail Moment, means applied to each condition tested. This parameter provides information on the degree of DNA damage: the higher it is, the greater the DNA damage.

Results:

The results are presented in FIGS. 2a and 2b. FIG. 2a shows the Tail Moment of a comet assay performed on NHK cells. FIG. 2b shows the Tail Moment of a comet assay performed on NHEM cells.

For the NHK, it is observed that, in the presence of UVB, the Tail Moment is very high (170.27 compared with 1.66 in the control). This demonstrates the deleterious effects of UVB radiation on cell DNA. An equivalent result is observed in the NHEM cells. By contrast, when the peptide SEQ ID NO: 7 is applied in a pretreatment on the cells, before treatment by UVB radiation, a reduction is observed in the Tail Moment in the NHK, going from 170.27 in the UVB condition to 51.36 in the active agent+UVB condition, i.e. a 70% reduction. A 55% reduction is observed in the NHEM cells.

Conclusions:

The results of these comet assays confirm those obtained in the microarray assay. The peptide compound SEQ ID NO: 7 made it possible to have a protective action on the cell DNA and, in general, has a protective action against oxidative stresses.

EXAMPLE 5

Composition of a Sun Cream

| Trade names | INCI names | % by weight |
|---|---|---|
| | PHASE A | |
| Demineralized water | Aqua (Water) | qs |
| PEMULEN™ TR1 | Acrylates/C10-30 Alkyl Acrylate Crosspolymer | 0.40 |
| Glycerin | Glycerin | 3.00 |
| NIPAGIN® M | Sodium Methylparaben | 0.3 |
| | PHASE B | |
| PARSOL® MCX | Ethylhexyl Methoxycinnamate | 7.50 |
| EUSOLEX® 4360 | Benzophenone-3 | 3.00 |
| PARSOL® 1789 | Butyl Methoxydibenzoylmethane | 2.00 |
| MYRITOL® 318 | Caprylic/Capric Triglyceride | 4.00 |
| EMULGADE® SEV | Hydrogenated Palm Glycerides (and) Ceteareth-20 (and) Ceteareth-12 (and) Cetearyl Alcohol | 5.00 |
| PHENOZETOL® | Phenoxyethanol | 0.5 |
| NACOL® 16-98 | Cetyl Alcohol | 1.00 |
| | PHASE C | |
| TEA | Triethanolamine | 0.20 |
| | PHASE D | |
| Peptide SEQ ID NO:4 | | 3 ppm |
| Parfum (Fragrance) | Fragrance | qs |
| Dye | | qs |

Applicants incorporate by reference the material contained in the accompanying computer readable Sequence Listing entitled "11-149_Sequence_Listing.txt", which was created on Oct. 10, 2013, and is 1,777 bytes in size.

The invention claimed is:

1. A peptide compound having one of the following sequences selected from the group consisting of:

Ser-Cys-Arg-Asp-Leu-Lys-Lys-Thr-NH$_2$; (SEQ ID NO: 1)

Asn-Ser-Ser-Lys-Asp-Leu-Lys-Lys-Phe-Val-Ala-NH$_2$ (SEQ ID NO: 2)

Cys-Lys-Asp-Leu-Lys-Lys-Ser-Phe; (SEQ ID NO: 3)

Gln-Thr-Arg-Asp-Leu-Lys-Lys-Ser-Pro-Lys-Val-NH$_2$; (SEQ ID NO: 4)

Asn-Lys-Asp-Leu-Lys-Lys-Pro-Met; (SEQ ID NO: 5)

His-Asp-Leu-Lys-Lys-Tyr-NH$_2$; (SEQ ID NO: 6)

or

Asp-Leu-Lys-Lys-NH$_2$. (SEQ ID NO: 7)

2. The peptide compound of claim 1, wherein the peptide compound is solubilized in one or more physiologically acceptable solvents, selected from the group consisting of water, glycerol, ethanol, propanediol, butylene glycol, dipropylene glycol, ethoxylated or propoxylated diglycols, cyclic polyols, and mixtures thereof.

3. A cosmetic composition comprising: a peptide compound, as an active principle, selected from the group consisting of:

```
                                        (SEQ ID NO: 1)
Ser-Cys-Arg-Asp-Leu-Lys-Lys-Thr-NH2;

(SEQ ID NO: 2)
Asn-Ser-Ser-Lys-Asp-Leu-Lys-Lys-Phe-Val-Ala-NH2;

(SEQ ID NO: 3)
Cys-Lys-Asp-Leu-Lys-Lys-Ser-Phe;

(SEQ ID NO: 4)
Gln-Thr-Arg-Asp-Leu-Lys-Lys-Ser-Pro-Lys-Val-NH2;

(SEQ ID NO: 5)
Asn-Lys-Asp-Leu-Lys-Lys-Pro-Met;

(SEQ ID NO: 6)
His-Asp-Leu-Lys-Lys-Tyr-NH2;

(SEQ ID NO: 7)
Asp-Leu-Lys-Lys-NH2;
``` and combinations thereof.

4. The composition of claim 3, wherein the composition is a topical composition comprising a cosmetically acceptable medium.

5. The composition of claim 3, wherein said peptide compound is present in the composition at a concentration of between around 0.0005 and 500 parts per million (ppm).

6. The composition of claim 5, further comprising at least one other active principle agent selected from the group consisting of plant peptide hydrolysates, other peptide compounds, sunscreens, anti-free radical agents, anti-wrinkle agents, and combinations thereof.

7. A method for cosmetic treatment of skin, the method comprising:
applying a composition comprising: a peptide compound, as an active principle, having one of the following sequences selected from the group consisting of:
(SEQ ID NO: 1) Ser-Cys-Arg-Asp-Leu-Lys-Lys-Thr-NH$_2$;
(SEQ ID NO: 2) Asn-Ser-Ser-Lys-Asp-Leu-Lys-Lys-Phe-Val-Ala-NH$_2$
(SEQ ID NO: 3) Cys-Lys-Asp-Leu-Lys-Lys-Ser-Phe;
(SEQ ID NO: 4) Gln-Thr-Arg-Asp-Leu-Lys-Lys-Ser-Pro-Lys-Val-NH$_2$;
(SEQ ID NO: 5) Asn-Lys-Asp-Leu-Lys-Lys-Pro-Met;
(SEQ ID NO: 6) His-Asp-Leu-Lys-Lys-Tyr-NH$_2$; or
(SEQ ID NO: 7) Asp-Leu-Lys-Lys-NH$_2$, and combinations thereof, and
a cosmetically acceptable medium.

8. The method of claim 7, wherein applying the composition comprises the application of a protective layer on the skin acting against ultraviolet (UV) radiation.

9. The method of claim 7 comprising treating age-related pigmentation defects and the effects of photoaging on the skin.

10. The method of claim 9, wherein the age-related pigmentation defects comprise age spots, solar lentigines, depigmentation spots, or freckles.

11. The method of claim 7 comprising treating skin tone irregularities and unifying skin tone.

12. The method of claim 7, wherein applying the composition comprises a morning application and an evening application.

13. The method of claim 7, wherein applying the composition comprises a before sun exposure application thereof, as before-sun care, or an after sun exposure application thereof, as after-sun care.

14. The composition of claim 3, wherein the peptide compound is solubilized in one or more physiologically acceptable solvents, selected from the group consisting of water, glycerol, ethanol, propanediol, butylene glycol, dipropylene glycol, ethoxylated or propoxylated diglycols, cyclic polyols, and mixtures thereof.

15. The composition of claim 3, wherein said peptide compound is present in the composition at a concentration of between around 0.01 and 5 parts per million (ppm).

16. The method of claim 7, wherein the cosmetic treatment further comprises attenuating age-related pigmentation defects and the effects of photoaging on the skin.

17. The method of claim 7, wherein the skin has age-related pigmentation defects.

18. The method of claim 7, wherein the skin has premature aging caused by exposure to the sun.

* * * * *

SEQUENCE LISTING

```
<160> NUMBER OF SEQ ID NOS: 7

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (8)..(8)
<223> OTHER INFORMATION: AMIDATION

<400> SEQUENCE: 1

Ser Cys Arg Asp Leu Lys Lys Thr
1               5

<210> SEQ ID NO 2
<211> LENGTH: 11
<212> TYPE: PRT
<213> ORGANISM: Artificial Sequence
<220> FEATURE:
<223> OTHER INFORMATION: Synthetic peptide

<400> SEQUENCE: 2

Asn Ser Ser Lys Asp Leu Lys Lys Phe Val Ala
1               5                   10

<210> SEQ ID NO 3
<211> LENGTH: 8
<212> TYPE: PRT
<213> ORGANISM: Artificial Sequence
<220> FEATURE:
<223> OTHER INFORMATION: Synthetic peptide

<400> SEQUENCE: 3

Cys Lys Asp Leu Lys Lys Ser Phe
1               5

<210> SEQ ID NO 4
<211> LENGTH: 11
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MOD_RES
<222> LOCATION: (11)..(11)
<223> OTHER INFORMATION: AMIDATION

<400> SEQUENCE: 4

Gln Thr Arg Asp Leu Lys Lys Ser Pro Lys Val
1               5                   10

<210> SEQ ID NO 5
<211> LENGTH: 8
<212> TYPE: PRT
<213> ORGANISM: Artificial Sequence
<220> FEATURE:
<223> OTHER INFORMATION: Synthetic peptide

<400> SEQUENCE: 5

Asn Lys Asp Leu Lys Lys Pro Met
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: AMIDATION

<400> SEQUENCE: 6

His Asp Leu Lys Lys Tyr
1               5

<210> SEQ ID NO 7
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: AMIDATION

<400> SEQUENCE: 7

Asp Leu Lys Lys
1
```